United States Patent [19]
Kaiserman et al.

[11] Patent Number: 5,338,474
[45] Date of Patent: Aug. 16, 1994

[54] SYSTEM FOR RELEASING BLEACH FROM A BLEACH PRECURSOR IN THE WASH USING AN ENZYME ACTIVATOR

[75] Inventors: Howard B. Kaiserman, Guttenberg; Daniel J. Kuzmenka, Lyndhurst, both of N.J.

[73] Assignee: Lever Brothers Company, Division of Conopco, Inc., New York, N.Y.

[21] Appl. No.: 841,395

[22] Filed: Feb. 25, 1992

[51] Int. Cl.$^5$ ............ C11D 3/395; C11D 17/00; C01B 15/10
[52] U.S. Cl. ............ 252/95; 252/174.12; 252/186.42; 252/186.38; 252/186.26; 252/DIG. 12
[58] Field of Search ............ 252/186.42, 186.38, 252/186.1, 174.12, 95

[56] References Cited

U.S. PATENT DOCUMENTS

| | | | |
|---|---|---|---|
| 3,974,082 | 8/1976 | Weyn | 252/95 |
| 4,861,509 | 8/1989 | Cornelissen et al. | 252/174.12 |
| 4,873,016 | 10/1989 | Thom et al. | 252/174.12 |
| 5,030,240 | 7/1991 | Wiersema et al. | 8/111 |
| 5,225,102 | 7/1993 | Coyne et al. | 252/186.26 |
| 5,230,822 | 7/1993 | Kamet et al. | 252/174.13 |

FOREIGN PATENT DOCUMENTS 0359087  3/1990  European Pat. Off.

Primary Examiner—Richard D. Lovering
Assistant Examiner—Joseph D. Anthony
Attorney, Agent, or Firm—Ronald A. Koatz

[57] ABSTRACT

The present invention provides a system for releasing a peracid from a peroxygen bleach source using a lipase enzyme as the activator.

6 Claims, No Drawings

SYSTEM FOR RELEASING BLEACH FROM A BLEACH PRECURSOR IN THE WASH USING AN ENZYME ACTIVATOR

BACKGROUND OF THE INVENTION

The present invention relates to a system for releasing bleach into a wash from a bleach precursor found in the wash (e.g., a diacyl peroxide) using enzymes as activators of the bleach precursors.

Various bleaches have long been employed in numerous cleaning applications including the washing and prewashing of fabrics as well as in other applications such as hard surface cleaning. In these applications, the bleaching agent oxidizes various stains or soils on fabrics, textiles and hard surfaces.

Peroxygen bleaching compounds such as hydrogen peroxide, sodium percarbonate and sodium perborate have been found useful in dry bleach formulations because of their oxidizing power. Other peroxygen compounds which supply oxidizing power include diacyl peroxides such as benzoyl peroxide.

Since peracids (the by-product of hydrolysis of the diacyl peroxide compounds) are difficult to stabilize and further since the peracids, if not stabilized, will attack enzymes and other compounds in solution susceptible to oxidative degradation, the oxidizing power of the diacyl peroxide compounds is protected by keeping them in the form of precursors.

Generally, the oxidizing power of the diacyl peroxide compound is released through the help of an activator in the wash. For example, activators such as perborate are known to react with benzoyl peroxides to result in the formation of perbenzoic acid.

A second way (other than bleach activators) of generating a peracid in the wash is to directly react an ester substrate (e.g., the peroxygen compound) with a perhydrolysis source. This mechanism is disclosed in EP 0,359,087. Such a perhydrolysis source is non-functional other than to activate the bleach precursor.

Another problem with this second approach is that the perhydrolysis source can itself destabilize other compounds of the composition.

Thus, the prior art teaches systems for generating peracids which either rely on expensive activators or which rely on supplying a non-functional and often destabilizing perhydrolysis source.

Accordingly, there is a need in the art for activating peroxygen source without using additional and expensive activator compounds and, preferably, with a compound which is already going to be used in the composition.

Further there is a need in the art for an activator compound which can release a peroxygen source under relatively mild conditions.

Unexpectedly, applicants have discovered a system whereby a peracid can be generated from a peroxygen source utilizing a component which will also be used for cleaning, i.e., an enzyme. The enzyme serves the dual purpose of activating the peroxygen source and providing detergent performance. Further, the enzyme has been found to activate under relatively mild pH conditions.

The present system may be used in liquid or powder detergent systems such as are well known to those skilled in the art.

BRIEF SUMMARY OF THE INVENTION

The subject invention provides a system for releasing a peracid from a peroxygen bleach source using esterase enzymes and, in particular, lipase enzymes. The use of the lipase enzymes allows the enzymes to function as activators of the peroxygen bleach source as well as providing the performance benefit associated with the use of lipase enzymes. The system further allows a peracid to be formed in the absence of a perhydrolysis source and under relatively mild pH conditions.

In particular, the bleaching system comprises
(1) a peracid bleach precursor; and
(2) an esterase enzyme for hydrolyzing the peracid bleach precursor in order to form a peracid compound.

The bleaching effect noted by the use of lipase enzymes on the peroxygen bleach substrate is enhanced further by the use of fine particles.

DETAILED DESCRIPTION OF THE INVENTION

The present invention relates to a system for releasing a peracid from a peroxygen bleach source using an esterase enzyme. Thus, the peracid is formed in the absence of a perhydrolysis source and under relatively mild conditions. In addition the enzyme has a dual activation/performance function and no additional activators are required.

The necessary components for the enzymatic (i.e., with an esterase) hydrolysis system of the invention are simply the peracid bleach precursor substrate and the esterase. Additional components which may be used in the system of the invention are adjuncts which may be of importance in a commercial product or process employing the invention.

Characteristics and preferred examples of the essential components of the enzymatic hydrolysis system, including the peracid bleach precursor substrate and the esterase, are discussed in greater detail below, followed by a discussion of other adjuncts which can be used together with the hydrolysis system and a number of examples which follow.

Ester Substrate (Peroxygen Bleach Precursor)

The bleach precursor (i.e., the ester substrate) of the invention can be any diacyl peroxide such as may be known to those skilled in the art and which is susceptible to enzymatic cleavage by the esterases of the invention.

More specifically, the substrate is a diacyl peroxide having the following structure:

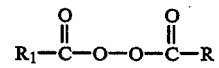

wherein R or $R_1$ may be the same or different and may be saturated or unsaturated alkyl having 1 to 20 carbons, an aryl group (e.g., phenyl group), or an alkaryl group (e.g., substituted phenyl group).

Most preferably, R and $R_1$ are phenyl groups and the component is a benzoyl peroxide derivative.

In general, there is a particle size dependence on bleaching performance such that the smaller the particle size (i.e., 1–300 microns, preferably 1–100 microns, most preferably less than 10 microns), the greater the bleaching effect. While not wishing to be bound by theory, this is believed to be associated with the fact that smaller particles have greater surface area and will more readily solubilize to interact with the esterase in the wash thereby releasing more of the available bleach.

Enzyme

While in principal any esterase which reacts with the ester substrate to produce enhanced bleaching may be used, those esterases which have been found to effectively function as bleach activators are fungal lipases producible by *Humicola languinosa* and *Thermomyces languinosus*.

An example of a fungal lipase as defined above is the lipase ex *Humicola languinosa*, available from Amano under the trade-name Amano CE; the lipase ex *Humicola languinosa* as described in the aforesaid European Patent Application No. 0258,068 (NOVO), as well as the lipase obtained by cloning the gene from *Humicola languinosa* and expressing this gene in *Aspergillus oryzae*, commercially available from NOVO Industry A/S under the trade name "Lipolase". The Lipolase is a preferred lipase for use in the present invention.

The lipases of the present invention are included in the liquid detergent composition in such an amount that the final composition has a lipolytic enzyme activity of from 100 to 0.005 LU/mg., preferably 25 to 0.05 LU/mg of the composition.

A Lipase Unit (LU) is that amount of lipase which produces 1 $\mu$mol of titratable fatty acid per minute in a pH stat. under the following conditions: temperature 30° C.; pH=9.0; substrate is an emulsion of 3.3 wt. % of olive oil and 3.3 % gum arabic, in the presence of 13 mmol/l $Ca^{2+}$ and 20 mmol/l NaCl in 5 mmol/l Trisbuffer.

Naturally, mixtures of the above lipases can be used. The lipases can be used in their non-purified form or in a purified form, e.g., purified with the aid of well-known adsorption methods, such as phenyl sepharose adsorption techniques.

The Bleach Release System Reaction

The invention is based on the interaction of the bleach substrate (i.e., preferably a diacyl peroxide) and an esterase (preferably a lipase enzyme).

The reaction takes place in the absence of any non-enzymatic bleach "activator" (since it is the enzyme which is activating) and in the absence of any perhydrolysis source.

Preferably, the reaction utilizes peracid bleach precursor particles from 1-300 microns, preferably 1-100 microns, most preferably under 10 microns in size.

It should be noted that the system can be used at a variety of pH levels. Thus, the system would be useful in normally basic aqueous solutions, in relatively neutral solutions and even in acidic solutions. The use of a buffer is possible but not necessary with the system.

The bleach release system is also adapted for a wide variety of temperatures as long as the temperatures do not denature the enzyme. Accordingly, the system of the invention may be employed in low temperature wash conditions as well as high temperature conditions.

An example of the bleach release system of the invention (using a diacyl peroxide substrate) is set forth schematically below.

In a preferred embodiment, the bleach release system shown as set forth below:

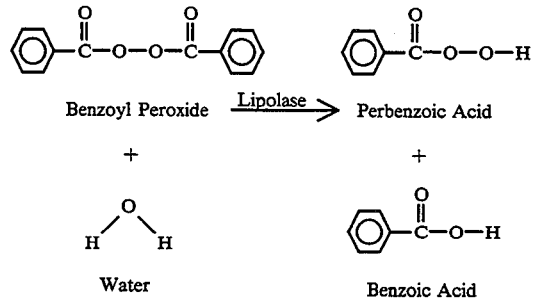

Other Adjuncts

The use of emulsifiers or surfactants is generally desirable as in other peracid bleach products, for example, to promote detergency and other characteristics desirable in such products. In addition, the emulsifying agents may or may not enhance bleach release. Accordingly, they are not considered essential to this invention.

Nonionic surfactants which may be used in the system of the invention include linear ethoxylated alcohols such as those sold by Shell Chemical Company under the brand name NEODOL ™. Other nonionic surfactants include various linear ethoxylated alcohols with an average length of from about 6 to 16 carbon atoms and averaging about 2 to 20 moles of ethylene oxide per mole of alcohol; linear and branched primary and secondary ethoxylated, propoxylated alcohols with an average length of about 6 to 16 carbon atoms and averaging 0 to 10 moles of ethylene oxide and about 1 to 10 moles of propylene oxide per mole of alcohol; linear and branched alkylphenoxy (polyethoxy) alcohols, otherwise known as ethoxylated alkylphenols with an average chain length of 8 to 16 carbon atoms and averaging 1.5 to 30 moles of ethylene oxide per mole of alcohol; and mixtures thereof.

Additional nonionic surfactants include certain block copolymers of propylene oxide and ethylene oxide, block polymers propylene oxide and ethylene oxide with propoxylated ethylene diamine, and semi-polar nonionic surfactants such as amine oxides, phosphate oxides, sulfoxides and their ethoxylated derivatives.

Anionic surfactants may also be employed. Examples of such anionic surfactants include alkali metal and alkaline earth metal salts of $C_4$ to $C_{18}$ fatty acids and resin acids, linear and branched alkyl benzene sulfonates, alkyl sulfates, alkyl ether sulfates alkane sulfonates, olefin sulfonates and hydroxyalkane sulfonates.

Suitable cationic surfactants include the quaternary ammonium compounds in which typically one of the groups linked to the nitrogen atoms is a $C_6$ to $C_{19}$ alkyl group and the other three groups are short chained alkyl groups which may bear inert substituents such as phenyl groups.

Further, suitable amphoteric and zwitterionic surfactants which may contain an anionic water-solubilizing group, a cationic group, and a hydrophobic organic group, include amino carboxylic acids and their salts, amino dicarboxylic acids and their salts, alkybetainoic, alkyl aminopropylbetains, sulfobetaines, alkyl imidazolinium derivatives, certain quaternary ammonium compounds, and certain tertiary sulfonium compounds.

Other exemplary emulsifiers include water soluble or dispersible polymers such as polyvinyl alcohol (PVA) polyvinylpyrrolidone (PVP), methylhydroxypropylcellulose (MHPC) etc., as well as bile and other natural emulsifiers.

Additional adjuncts of a wide variety may be considered for use in combination with the bleach release system of the present invention, depending upon the specific application contemplated. For example, as noted above, the bleach release system may be employed or included within a wide variety of cleaning applications or formulations such as straight bleach products, pre-wash products (which are often in liquid form) and even various hard surface cleaners.

Builders which can be used according to the invention include any of the many builders used in the amounts specified for structured or unstructured liquids (if the composition is liquid rather than powder) as described in U.S. Pat. No. 5,071,586 to Kaiserman et al, which is hereby incorporated by reference into the subject application. By structured liquid composition is meant a composition in which at least some of the detergent active forms a structured phase capable of suspending a solid particulate material. Greater details are provided in the aforementioned Kaiserman patent.

Additional adjuncts may include fragrances, dyes, stabilizers, buffers, etc. Stabilizers may be included to achieve a number of purposes. For example, the stabilizers may be directed toward establishing and maintaining effectiveness of the enzymes for original formulation components or even intermediate products existing after the formulation is placed in an aqueous solution. Since enzymes may be hindered in hydrolysis of the substrates because of heavy metals, organic compounds, etc., for example, suitable stabilizers which are generally known in the prior art may be employed to counter such effects and achieve maximum effectiveness of the enzymes within the formulations.

Examples of such enzyme stabilization systems include, but are not limited to calcium salts such as $CaCl_2$; short chain carboxylic acids or salts thereof, such as formic acid or propionic acid; polyethylene glycols, various polyols and specific hydrolyzed protein. Examples of suitable enzyme stabilizers are disclosed in U.S. Pat. Nos. 4,518,694; 4,908,150; and 4,011,169; all of which are incorporated herein by reference.

Buffering agents can also be utilized in the invention to maintain a desired alkaline pH level for the aqueous solutions. Buffering agents generally include all such materials which are well known to those skilled in the detergent art. In particular, buffering agents contemplated for use in the present invention include but are not limited to carbonates, phosphates, silicates, borates and hydroxides.

Another optional ingredient which may be used, particularly in structured liquids, is a deflocculating polymer such as is described in U.S. Pat. No. 5,071,586 to Kaiserman et al. or in U.S. Pat. No. 4,992,194 to Liberati et al., both of which are incorporated by reference into the subject application.

The following examples are intended to illustrate the invention further and are not intended to limit the claims in any way.

Experimental Conditions

The bleaching results discussed below where obtained by testing the bleach release system (i.e., enzyme substrate and enzyme) either alone or together under various conditions in a tergotometer containing a base solution set forth below:

|  | Percentage by Weight |
|---|---|
| Sodium Alkyl Benzene Sulfonate | 21.0 |
| Neodol 25-7 ($C_6$-$C_{20}$ fatty alcohol alkoxylated with about 7 moles alkylene oxide | 9.0 |
| Glycerol | 3.5 |
| Sodium Metaborate | 2.6 |
| Sodium Citrate | 9.21 |
| Dequest 2060S* | 0.4 |
| Calcium Chloride | 0.15 |
| Decoupling Polymer ** | 1.0 |
| Compression Polymer *** | 0.2 |
| Water to | 100% |

\* Diphosphonic acid sequestering agent.
\*\* Copolymer of acrylic acid and lauryl methacrylate having molecular weight of about 4,000.
\*\*\* Polyacrylic acid of MW about 50,000.

The tergotometer is designed to agitate the wash solution in a manner representative of a commercial washing machine. A test material is agitated in the tergotometer for a specified period of time at specified conditions to observe bleaching results. Typically, terge conditions are defined at 40° C. for 15 minutes and using water having 120 ppm hardness. Generally, the ratio of hardness ions is about 2:1 calcium to magnesium.

Bleaching is generally indicated by an increase in reflectance after washing (e.g., as measured on a Colorgard system/05 Reflectometer), reported as R. If the substrate material is a tea stain, as in the present example, the reflectance value is typically measured on a tea-stained cloth or BC-1 cloth. Thus change in reflectance on the cloth is measured in BC-1 units. Of course, as defined above, the difference in reflectance value of a tea-stained cloth washed with the bleach release system of the invention versus a cloth washed in the base solution (without bleach release system) is measured as R and this is also measured in BC-1 units. More precisely:

$$\Delta R = REFLECTANCE_{(FINAL)} - REFLECTANCE_{(INITIAL)}$$

$$\Delta\Delta R = R_{BLEACHING\ AGENT} - \Delta R_{BASE} = BLEACHING\ PERFORMANCE$$

EXAMPLE 1

About 0.15 grams of benzoyl peroxide was added to a base composition in a tergotometer as defined above and under conditions defined above (40° C., 15 minutes, 120 ppm hardness). The benzoyl peroxide was added alone (Examples 2 and 3) and with varying amounts of lipase enzyme (Examples 4–7). Example 4 utilizes benzoyl peroxide having 850 micron particle size and examples 5–7 utilize benzoyl peroxide having less than 10 micron particle size.

The results of these tests are set forth in Table I below:

TABLE I

| Components | Comparative Examples | | | | | | |
|---|---|---|---|---|---|---|---|
|  | 1 | 2 | 3 | 4 | 5 | 6 | 7 |
| Base | + | + | + | + | + | + | + |
| Benzoyl Peroxide (850 microns) | − | + | − | + | − | − | − |
| Benzoyl Peroxide (<10 microns) | − | − | + | − | + | + | + |
| Lipolase (25 μl) | − | − | − | + | + | − | − |
| Lipolase (250 μl) | − | − | − | − | − | + | − |
| Lipolase (500 μl) | − | − | − | − | − | − | + |

TABLE I-continued

| Components | Comparative Examples | | | | | | |
|---|---|---|---|---|---|---|---|
| | 1 | 2 | 3 | 4 | 5 | 6 | 7 |
| ΔΔ R | — | 0 | 2.4 | 0.3 | 4.4 | 6.1 | 6.5 |

As can be clearly seen from Table I above, utilizing small particle size substrate significantly enhances the enzyme effect on bleach release.

As further seen from Table I, the concentration of the enzyme also has an effect on bleaching (i.e., ΔΔR of 6.1 and 6.5 for 250 µl and 500 µl, respectively versus 4.4 for 25 µl) in three systems having a substrate of comparable particle size.

EXAMPLE 2

Benzoyl peroxide bleach precursor (BP) substrate was tested on BC-1 cloth in a tergotometer under cold water conditions using lipase enzyme. These results are set forth below.

| Components | ΔΔ R |
|---|---|
| Base | — |
| Base + BP | 0.5 |
| Base + BP + Lipase | 4.8 |

Conditions: 20° C., 150 PPM, BP (less than 10 microns), pH 8, 50 µL Lipolase 100L These results show that the bleach release system of the invention can be used in cold water conditions (i.e., 20° C.) as well as hot water conditions.

EXAMPLE 3

Benzoyl peroxide bleach precursor substrate (BP) was tested on BC-1 cloth in a tergotometer at 40° C. using 150 ppm BP (having a particle size of less than 10 microns) and using 50 µl of Lipolase 100 L enzyme under varying pH ranges. The following results were observed.

| Component | ΔΔ R at Varying pH | | | |
|---|---|---|---|---|
| | pH 7 | pH 8 | pH 9 | pH 10 |
| Base | — | — | — | — |
| Base & BP | 1.2 | 2.2 | 6.1 | 8.4 |
| Base & BP & Lipolase 100L | 3.0 | 4.0 | 7.2 | 8.3 |

This example shows that the bleach release system clearly provides beneficial bleaching range over a broad range of pH values and can be used in a wide variety of compositions.

EXAMPLE 4

Lipolase enzyme was used on various diacyl peroxide bleach precursor substrates in a tergotometer at 40° C. and 150 ppm substrate and the results are set forth below:

| PEROXIDE SUBSTRATE | ΔΔ R TOTAL | ΔΔ R LIPOLASE |
|---|---|---|
| p-Mononitro Benzoyl + Lipolase | 7.0 7.2 | 0.2 |
| Benzoyl + Lipolase | 5.0 7.4 | 2.4 |
| m-Toluoyl + Lipolase | 1.9 4.3 | 2.4 |
| m-Anisoyl Benzoyl + Lipolase | 3.2 6.1 | 2.9 |
| p-Anisoyl Benzoyl + Lipolase | −0.3 2.7 | 3.0 |
| m-Monomethoxy Benzoyl₂ + Lipolase | 6.7 9.7 | 3.0 |
| m-Monomethyl Benzoyl₂ + Lipolase | 4.0 7.7 | 3.7 |
| p-Monomethyl Benzoyl₂ + Lipolase | −0.1 5.3 | 5.4 |

As can be seen from the results above, the lipase functions as a bleach activator using a variety of different diacylperoxide substrates.

EXAMPLE 5

Benzoyl Peroxide (BP) was tested with various enzymes and the following results were observed:

TABLE III

| Lipases | Total ΔΔ R (Due to Enzyme and BP) | ΔΔ R of Total Due to Enzyme |
|---|---|---|
| No enzyme | 2–4 | 0 |
| Fungal | | |
| *Humicola Languinosa* (Lipolase) | 8 | 4 |
| Liquid | 8 | 4 |
| Powder | 8 | 4 |
| T Granule | 8 | 4 |
| Heat Killed | 4 | 0 |
| *Aspergillus Niger* | 6.3 | 3.9 |
| *Mucor Miehei* | 4.0 | 1.6 |
| *Candida Cylindracea* | 4.2 | 1.3 |
| *Rhizopus Arrhizus* | 4 | 0 |
| Bacterial | | |
| *Pseudomonas Gladioli* | 4 | 0 |
| *Pseudomonas Cepacia* | 4 | 0 |
| Esterases Mammalian | | |
| Porcine Liver | 4.0 | 0 |
| Rabbit Liver | 4.0 | 0 |
| Proteases Bacterial | | |
| Savinase | 4.0 | 0 |
| Durazym | 4.0 | 0 |

Table III demonstrates enhanced bleaching provided by use of lipase enzyme activators used in conjunction with benzoyl peroxide.

We claim:

1. A composition for release of bleach peracid in the wash comprising:
   (a) peracid bleach precursor enzyme substrate which is a diacyl peroxide having the structure:

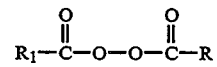

wherein R and $R_1$ are the same or different and are selected from the group consisting of saturated or unsaturated alkyl having 1 to 20 carbons, aryl and alkaryl; and
   (b) a lipase enzyme used in an amount such that the final composition has a lipolytic enzyme activity of from 100 to 0.005;
   wherein the lipase enzyme reacts with said enzyme substrate to release a peracid in the wash.

2. A composition according to claim 1, wherein the diacyl peroxide is benzoyl peroxide.

3. A composition according to claim 1, wherein the enzyme substrate has a particle size of 1–300 microns.

4. A composition according to claim 1, wherein the lipase enzyme is obtained by cloning the gene from *Humicola lanuginosa* and expressing the gene in *Aspergillus oryzae*.

5. A detergent composition comprising
   (1) 2–85% by weight detergent active; and
   (2) a composition for release of bleach peracid in the wash comprising:
      (a) peracid bleach precursor enzyme substrate which is a diacyl peroxide having the structure:

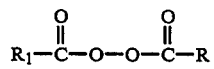

wherein R and $R_1$ are the same or different and are selected from the group consisting of saturated or unsaturated alkyl having 1 to 20 carbons, aryl and alkaryl; and
      (b) a lipase enzyme used in an amount such that the final composition has a lipolytic enzyme activity of from 100 to 0,005;
   wherein the lipase enzyme reacts with said enzyme substrate to release a peracid in the wash.

6. A composition according to claim 5 wherein the pH may vary from about 7 to about 10.

* * * * *